(12) United States Patent  
Nishiyama

(10) Patent No.: US 9,113,842 B2  
(45) Date of Patent: Aug. 25, 2015

(54) BIOLOGICAL INFORMATION MEASURING DEVICE AND ATTACHMENT METHOD THEREFOR

(71) Applicant: CASIO COMPUTER CO., LTD., Shibuya-ku, Tokyo (JP)

(72) Inventor: Hiroki Nishiyama, Fussa (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 91 days.

(21) Appl. No.: 13/787,701

(22) Filed: Mar. 6, 2013

(65) Prior Publication Data

US 2013/0237794 A1    Sep. 12, 2013

(30) Foreign Application Priority Data

Mar. 7, 2012    (JP) .................................. 2012-049973

(51) Int. Cl.
| | |
|---|---|
| *A61B 5/0408* | (2006.01) |
| *A61B 5/00* | (2006.01) |
| *A61B 5/0402* | (2006.01) |
| *A61B 5/024* | (2006.01) |
| *A61B 5/0245* | (2006.01) |
| *A61B 5/11* | (2006.01) |

(52) U.S. Cl.
CPC ............. *A61B 5/6802* (2013.01); *A61B 5/0245* (2013.01); *A61B 5/02438* (2013.01); *A61B 5/0402* (2013.01); *A61B 5/0408* (2013.01); *A61B 5/6823* (2013.01); *A61B 5/6831* (2013.01); *A61B 5/002* (2013.01); *A61B 5/11* (2013.01); *A61B 2560/0209* (2013.01); *A61B 2560/0475* (2013.01); *A61B 2562/14* (2013.01); *A61B 2562/224* (2013.01); *A61B 2562/227* (2013.01)

(58) Field of Classification Search
CPC .. A61B 5/0408; A61B 5/6802; A61B 5/6823; A61B 5/6831; A61B 2562/224
USPC ........................................................ 600/390
See application file for complete search history.

(56) References Cited

U.S. PATENT DOCUMENTS

| | | | | |
|---|---|---|---|---|
| 5,078,134 | A * | 1/1992 | Heilman et al. .................. | 607/4 |
| 6,272,365 | B1 * | 8/2001 | Ronkainen et al. ........... | 600/390 |
| 7,640,049 | B2 * | 12/2009 | Juan .............................. | 600/390 |
| 7,747,303 | B2 * | 6/2010 | Eichler ......................... | 600/390 |
| 2007/0276200 | A1 | 11/2007 | Ahola et al. | |
| 2008/0027345 | A1 | 1/2008 | Kumada et al. | |
| 2008/0058663 | A1 | 3/2008 | Fujiwara | |

FOREIGN PATENT DOCUMENTS

| | | | |
|---|---|---|---|
| JP | 63-049135 | A | 3/1988 |
| JP | 02-109604 | U | 9/1990 |
| JP | 05-212136 | A | 8/1993 |
| JP | 59-225037 | A | 12/1994 |
| JP | 2005-161025 | A | 6/2005 |
| JP | 2006-271659 | A | 10/2006 |
| JP | 4671406 | B2 | 4/2011 |

OTHER PUBLICATIONS

Chinese Office Action dated Sep. 1, 2014, issued in counterpart Chinese Application No. 201310146102.X.

* cited by examiner

*Primary Examiner* — Lee S Cohen

(74) *Attorney, Agent, or Firm* — Holtz, Holtz, Goodman & Chick PC

(57) ABSTRACT

A biological information measuring device provided with a belt which includes at least one electrode detecting a voltage based on biological information in accordance with contact between the at least one electrode and a human body; a supporting member which supports a tank where a predetermined fluid is stored; an attachment which attaches the belt to the supporting member and has a fluid supply portion supplying the fluid to the at least one electrode; and a biological information circuit which measures biological information based on the voltage detected by the at least one electrode.

15 Claims, 11 Drawing Sheets

IIC-IIC CROSS-SECTION

IIIC-IIIC CROSS-SECTION

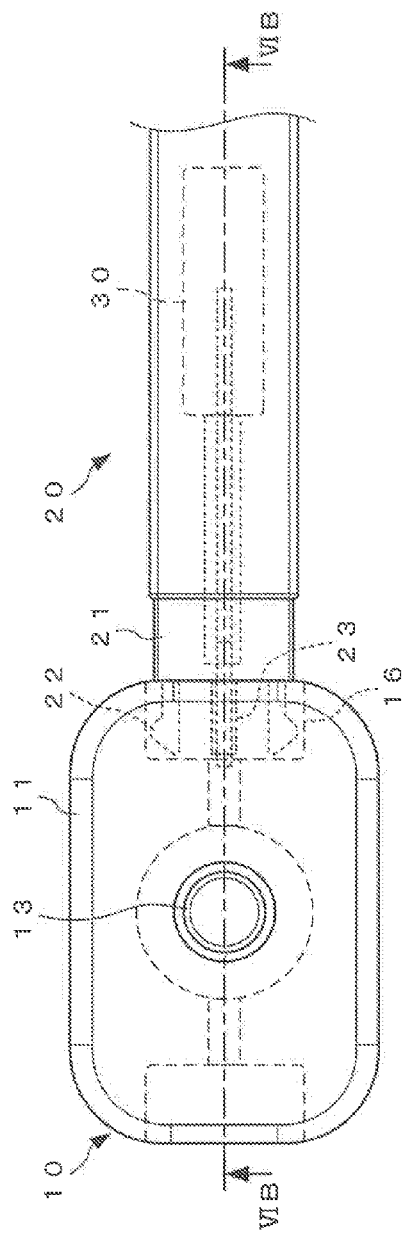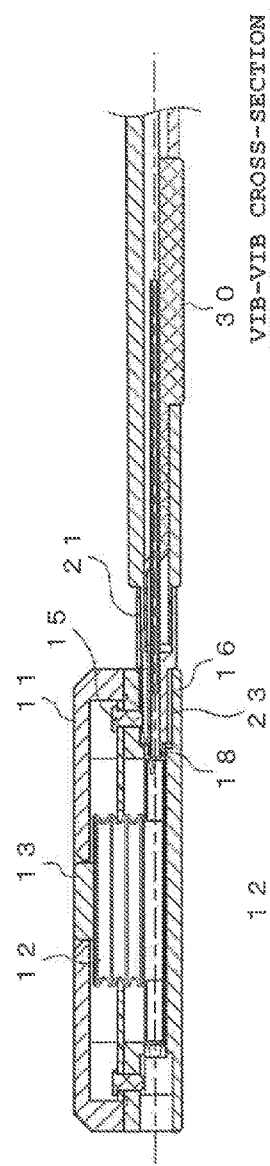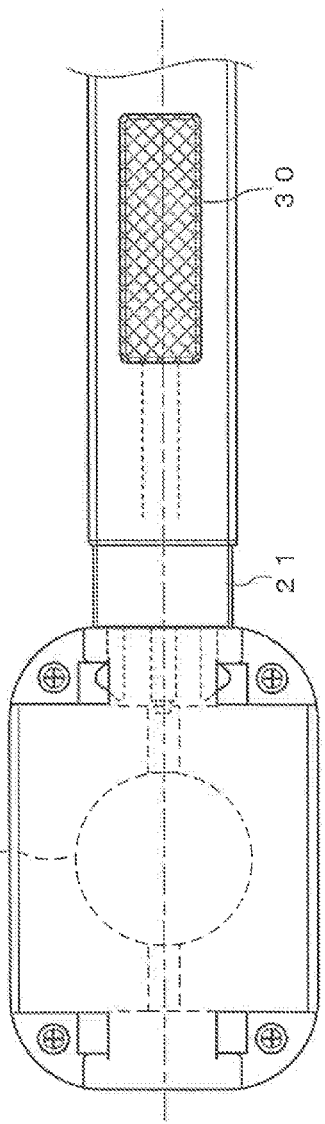

BIOLOGICAL INFORMATION MEASURING DEVICE AND ATTACHMENT METHOD THEREFOR

CROSS-REFERENCE TO RELATED APPLICATION

This application is based upon and claims the benefit of priority from the prior Japanese Patent Application No. 2012-049973, filed Mar. 7, 2012, the entire contents of which is incorporated herein by reference.

BACKGROUND OF THE INVENTION

1. Field of the Invention

The present invention relates to a biological information measuring device and an attachment method for the biological information measuring device. In particular, the present invention relates to a biological information measuring device that is attached to the chest area of a human body during physical exercise and measures biological information data, and an attachment method for the biological information measuring device.

2. Description of the Related Art

Recently, because of increased health consciousness, more people have maintained good health and cared for their state of health through daily exercise, such as running and walking. Such people tend to show a high interest in measuring and recording their state of health and exercise conditions by numerical values or data. For example, these people grasp their state of health and exercise conditions by measuring and recording the number of steps walked, the distance traveled, pulse, calories consumed, and the like using various measuring terminals, such as mobile terminals, wristwatches, pedometers.

As an example of such measuring terminals, Japanese Patent Application Laid-open (Kokai) Publication No. Showa 59-225037 and Japanese Patent Application Laid-open (Kokai) Publication No Heisei 05-212136 disclose a belt-type heart rate measuring device that is attached to the chest area. The heart rate measuring device has a configuration basically including: a belt for attaching to the chest area; a sensor section including a pair of electrodes arranged on the inner surface of the belt such that the pair of electrodes are placed in direct contact with the skin of the chest area; and a heart rate monitor or a heart rate display device for measuring the heart rate based on electrocardiographic signals detected by the sensor section. In Japanese Patent Application Laid-Open (Kokai) Publication No. Showa 59-225037 and Japanese Patent Application Laid-Open (Kokai) Publication No, Heisei 5-212136, the belt provided with the sensor section and the heart rate monitor or the heart rate display device for measuring the heart rate are separately configured. However, the heart rate monitor or the heart rate display device integrally provided in the belt is also known.

The above-described type of heart rate measuring device is configured to be attached by a stretchable belt being wound around the chest area of a measurement subject to measure the measurement subject's heart rate during exercise. In this structure, the electrodes provided on the inner surface of the belt are placed in direct contact with the chest area. However, to accurately and unfailingly acquire the electrocardiographic signals from the human body (subject's body), it is required to ensure sufficient electrical conductivity between the surface of the human body and the electrodes. Therefore, when the heart rate measuring device is attached, it is generally required to place the electrode sections in direct contact with the chest area in a state where the electrode sections are wetted or dampened by water or the like.

In this type of attachment method, there is a problem in that the measurement subject experiences unpleasantness because of unexpected coldness and discomfort when the temperature is low, particularly in the winter or the like. To avoid such unpleasantness, hot water or the like can be used to wet the electrode sections. However, even if the measurement subject attaches the heart rate measuring device in the above-described manner and actually starts exercising, the electrode sections may be dried because of moisture evaporation. In this case, sufficient electrical conductivity between the surface of the human body (subject's body) and the electrodes cannot be ensured from when the electrode sections are dried until the electrode sections become suitably wetted by perspiration from the measurement subject. Therefore, there is a problem in that accurate electrocardiographic signals cannot be acquired from the human body.

The above and further objects and novel features of the present invention will more fully appear from the following detailed description when the same is read in conjunction with the accompanying drawings. It is to be expressly understood, however, that the drawings are for the purpose of illustration only and are not intended as a definition of the limits of the invention.

SUMMARY OF THE INVENTION

In accordance with one aspect of the present invention, there is provided a biological information measuring device comprising a belt which includes at least one electrode detecting a voltage based on biological information in accordance with contact between the at least one electrode and a human body; a supporting member which supports a tank where a predetermined fluid is stored; an attachment which attaches the belt to the supporting member and has a fluid supply portion supplying the fluid to the at least one electrode; and a biological information circuit which measures biological information based on the voltage detected by the at least one electrode.

In accordance with another aspect of the present invention, there is provided an attachment method for a biological information measuring device, the biological information measuring device comprising: a belt which includes at least one electrode detecting a voltage based on biological information in accordance with contact between the at least one electrode and a human body; a supporting member which supports a tank stored a predetermined fluid; and an attachment which attaches the belt to the supporting member and has a fluid supply portion supplying the fluid to the at least one electrode, and the attachment method comprising: connecting the belt, the attachment and the supporting member to each other, winding the belt around the human body such that the electrode and the supporting member are placed in contact with the human body, and setting the electrode is set in a state where biological information is detectable, and setting the fluid within the tank in a state which is supplied to the electrode by connecting the electrode to the supporting member.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 6A to FIG. 6C are schematic diagrams of the attachment method (2) for the biological information measuring device according to the embodiment;

DETAILED DESCRIPTION OF THE PREFERRED EMBODIMENTS

A biological information measuring device and an attachment method for the biological information measuring device according to an embodiment of the present invention will hereinafter be described in detail.

(Biological Information Measuring Device)

Figure 1A:
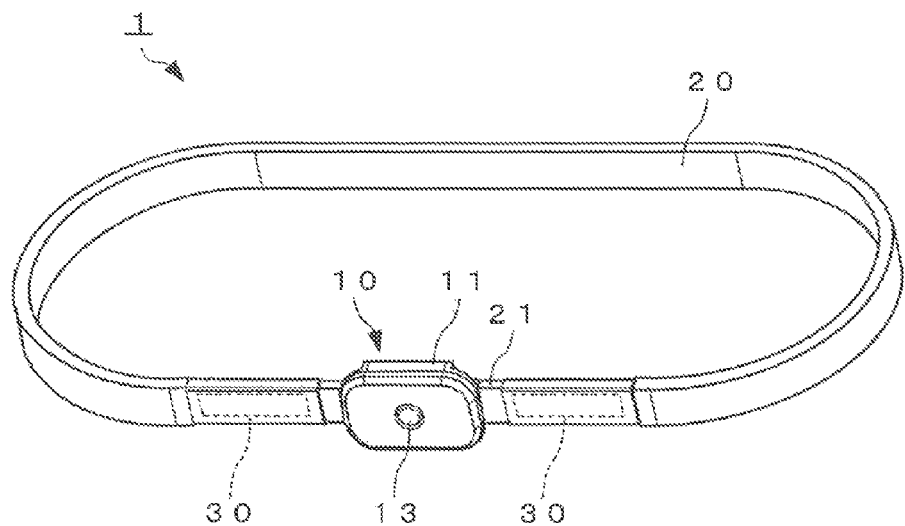
FIG. 1A and FIG. 1B are schematic diagrams of a biological information measuring device according to an embodiment of the present invention.
Figure 1B:
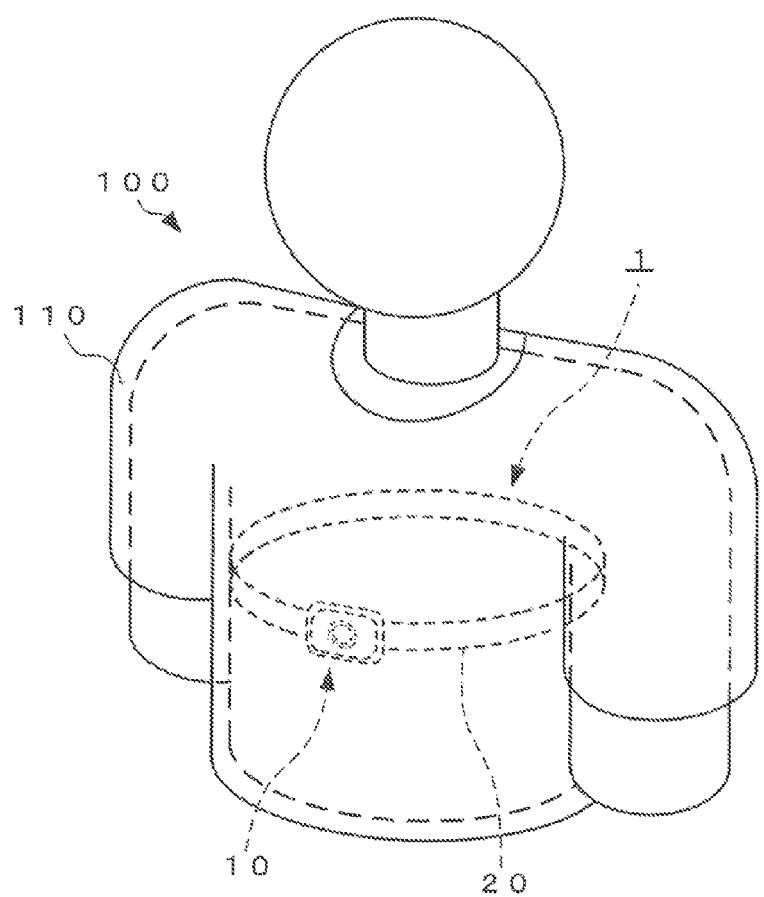

FIG. 1A and FIG. 1B are schematic diagrams of a biological information measuring device according to an embodiment of the present invention. Here, FIG. 1A is a perspective view of the biological information measuring device 1 according to the present embodiment. FIG. 1B is a schematic diagram showing a state where the biological information measuring device 1 according to the present embodiment attached to a human body.

The biological information measuring device 1 according to the present embodiment basically includes a supporting member 10; a belt 20 with stretch properties such that both ends of the belt 20 are detachably connected to the supporting member 10; and a pair of electrodes 30 provided on the inner surface side (the human-body side when attached) of the belt 20, as shown in FIG. 1A. The biological information measuring device 1 is directly attached to the chest area underneath the clothing 110 of a measurement subject 100 in a state where the belt 20 is wound around the chest area, as shown in FIG. 1B. At this time, the attachment position of the biological information measuring device 1 is adjusted such that the pair of electrodes 30 provided on the inner surface of the belt 20 is directly contacted in a suitable position of the chest area of the measurement subject 100. An adjuster (not shown in FIG. 1A and FIG. 1B) may be provided in the belt 20 to adjust the length of the belt 20 in accordance with the chest girth of the measurement subject 100.

Each configuration will hereinafter be described in detail.

Figure 2A:
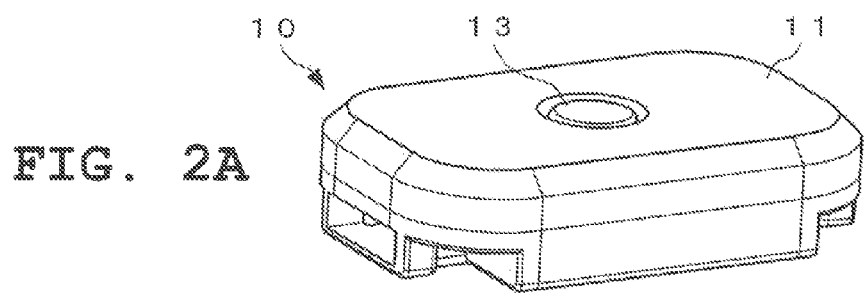
FIG. 2A to FIG. 2D are schematic diagrams of an example of a supporting member used in the biological information measuring device according to the embodiment.
Figure 2B:
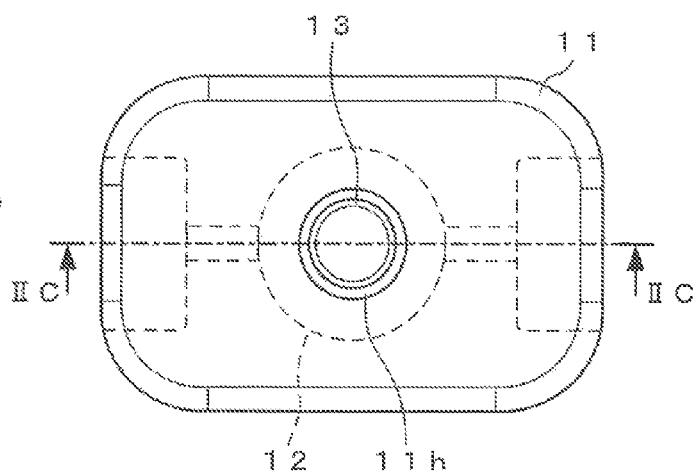
Figure 2C:
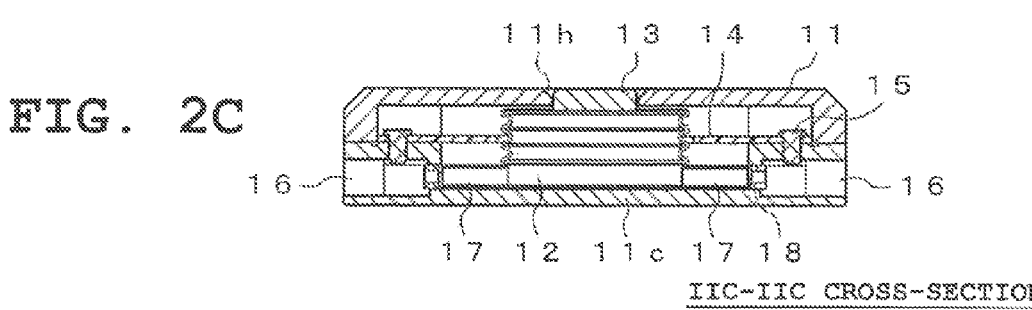
Figure 2D:
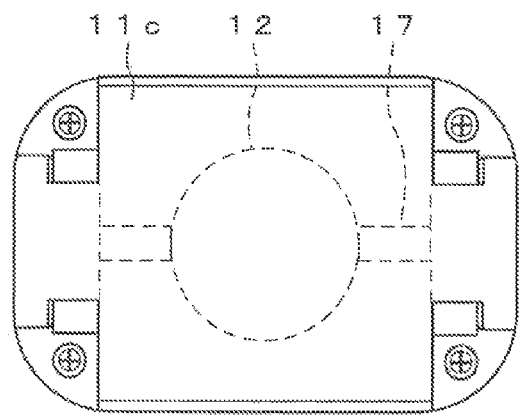

FIG. 2A to FIG. 2D are schematic diagrams of an example of the supporting member 10 used in the biological information measuring device 1 according to the present embodiment. Here, FIG. 2A is a perspective view of the supporting member 10 according to the present embodiment. FIG. 2B is a top view (front view) of the supporting member 10 according to the present embodiment. FIG. 2C is a cross-sectional view of the supporting member 10 according to the present embodiment. FIG. 2D is a bottom view (rear view) of the supporting member 10 according to the present embodiment. FIG. 2C shows a cross-sectional structure taken along line IIC-IIC shown in FIG. 2B (in the present specification, a Roman numeral "II" is used for convenience as a symbol corresponding to an Arabic numeral "2" shown in FIG. 2B).

The supporting member 10 is basically provided with: a main body 11 having a cuboid shape of which the corner portions are rounded or chamfered; a tank 12 having flexibility; a pressing section 13 (a pressure applying section) used for pressing the tank 12; a circuit board 14, connection terminals 15; engaging sections 16 to which attachments 21 provided on both ends of the belt 20 engage; pipes 17 communicating between the tank 12 and the engaging sections 16; and control valves 18, as shown, for example, in FIG. 1A, FIG. 1B, and FIG. 2A to FIG. 2D.

The pair of recessed engaging sections 16 is provided on the opposing side portions of the main body 11 (left and right side surfaces in FIG. 2C) such that the attachments 21 provided on both ends of the belt 20, described hereafter, engage with the pair of recessed engaging sections 16. The tank 12, the circuit board 14, the connection terminals 15, the pipes 17, and the control valve 18 are provided within the main body 11, and are stored by being enclosed with an enclosing cover 11c provided on the undersurface side of the main body 11. An opening section 11h is provided on the top surface of the main body 11 such that the pressing section 13 attached to the tank 12 is exposed. The enclosing cover 11c is formed with a high thermal conductive material or the like, and is attached and fixed to the main body 11 such that the enclosing cover 11c is in close contact with the tank 12, as shown in FIG. 2C. As a result, when the measurement subject 100 attaches the biological information measuring device 1 on the chest area, the body heat from the measurement subject 100 is transmitted through the enclosing cover 11c to a fluid within the tank 12 and the pipe 17, thereby increasing (heating) the temperature of the fluid to a temperature close to body temperature.

The tank 12 is composed of a soft resin member or the like, and a fluid is stored therein so as to wet the electrodes 30 provided on the inner surface side of the belt 20, described hereafter. The tank 12 has a cylindrical shape of which the side surface is formed into a bellows shape, as shown in FIG. 2C, for example. The pressing section 13 is provided on the top surface of the tank 12. The pair of pipes 17 are provided on portions of the side surfaces positioned in the bottom surface side such that the pair of pipes 17 extends towards the engaging sections 16. The tank 12 is preferably designed to have a relatively small capacity such that the temperature of the fluid stored within the tank 12 is favorably increased (heated) to a temperature close to body temperature by the body heat from the measurement subject 100, when the measurement subject 100 attaches the biological information measuring device 1 on the chest area as described above. Specifically, for example, the tank 12 is designed to hold an amount of fluid such that the electrodes 30 provided in the belt 20 can be suitably wetted by fluid supplied in a single operation of a fluid supplying operation described hereafter. Here, the fluid stored in the tank 12 is adjusted such that sufficient electrical conductivity can be ensured between the electrodes 30 and the chest area of the human body in a state where the electrodes 30 are wetted or dampened by the fluid, as described in detail hereafter. Specifically, tap water containing chlorine or an electrolytic solution containing a predetermined concentration of electrolyte, such as sodium, can be applied as the fluid. It is preferable that the fluid is easily available to the measurement subject 100.

The pressing section 13 is provided on the top surface of the tank 12, and is configured to be partially exposed from the opening section 11h provided on the top surface of the main body 11 of the supporting member 10, as shown in FIG. 2C. When the measurement subject 100 can press the pressing section 13 exposed on the top surface of the main body 11 in a state where the biological information measuring device 1 is attached to the chest area, external pressure is applied to the tank 12, and whereby the fluid stored within the tank 12 is pushed out through the pipes 17.

The circuit board 14 is at least provided with an electronic circuit. The electronic circuit detects biological information of the measurement subject 100 as an electric voltage variation pattern acquired by the pair of electrodes 30 provided in the belt 20, described hereafter, and then stores the detected biological information as biological information data. The electronic circuit also transmits the biological information data to an external device using a predetermined communication method. The configuration and functions of the electronic circuit contained in the supporting member 10 will be described in detail hereafter.

The connection terminals 15 are electrically connected to the electronic circuit provided on the above-described circuit board 14 and are provided such that the parts of the connection terminals 15 are respectively exposed within the recessed engaging sections 16 provided in the main body 11. The engaging sections 16 are configured such that the attachments 21 provided on both ends of the belt 20 are detachably connected to the engaging sections 16, as described in detail hereafter. As a result, the belt 20 can be arbitrarily attached to and detached from the supporting member 10. Furthermore, as well as the connection terminals 15, the pipes 17 communicating to the tank 12 and the control valves 18 are also exposed within the recessed engaging sections 16. When the attachments 21 of the belt 20 are respectively engaged with the engaging sections 16, the circuit board 14 is electrically connected to the electrodes 30 provided in the belt 20 through the connection terminals 15. In addition, the fluid stored in the tank 12 is set in a state which is supplied to the electrodes 30 provided in the belt 20, through the pipes 17 and the control valves 18. An attachment method for the biological information measuring device 1 will be described in detail hereafter.

Each of the pipes 17 is provided such that one end side of the pipes 17 is connected to the portion of the side surface positioned in the bottom surface side of the tank 12, and the other end side of the pipes 17 reaches into the engaging section 16. The pipes 17 are formed to respectively communicate between the tank 12 and the engaging sections 16. Each of the control valves 18 is provided on the other end side of the pipe 17 such that the control valves 18 is exposed within the engaging section 16. Here, the control valve 18 is opened and becomes in an open state only while the attachment 21 of the belt 20 is engaged with the engaging section 16. While the attachment 21 is not engaged with the engaging section 16, the control valve 18 is closed and becomes in a closed state.

As a result, the fluid within the tank 12 is supplied through the pipes 17 to the belt 20 only while the belt 20 is connected to the main body 11 of the supporting member 10, or in other words, while the biological information measuring device 1 is attached to the chest area of the measurement subject 100. In addition, the control valve 18 is closed while the belt 20 is not connected to the main body 11 of the supporting member 10. As a result, the fluid stored in the tank 12 does not leak out.

Figure 3A:
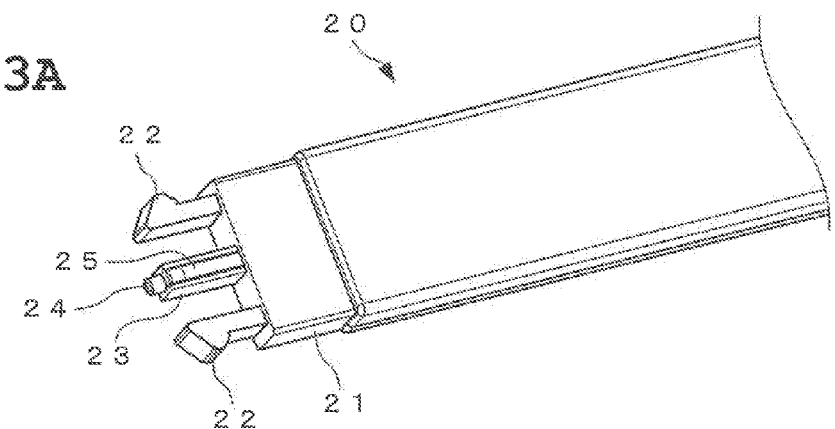
FIG. 3A to FIG. 3D are schematic diagrams of an example of a belt and electrodes used in the biological information measuring device according to the embodiment.
Figure 3B:
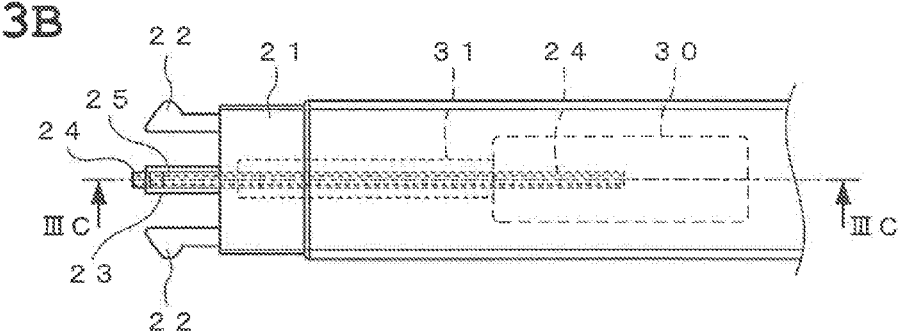
Figure 3C:
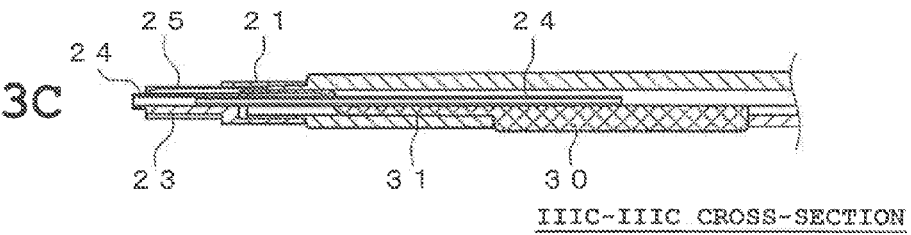
Figure 3D:
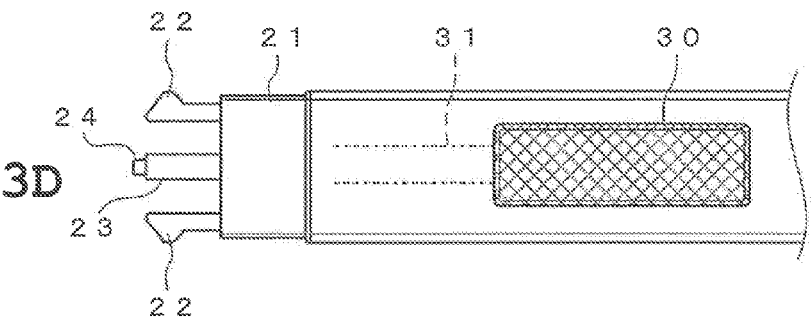

FIG. 3A to FIG. 3D are schematic diagrams of an example of the belt 20 and the electrodes 30 used in the biological information measuring device 1 according to the present embodiment. Here, FIG. 3A is a perspective view of a configuration of main sections of the belt 20 according to the present embodiment. FIG. 3B is a top (outer surface) view of the configuration of the main sections of the belt 20 according to the present embodiment. FIG. 3C is a cross-sectional view of the configuration of the main sections of the belt 20 according to the present embodiment. FIG. 3D is a bottom (inner surface) view of the configuration of main sections of the belt 20 according to the present embodiment. FIG. 3C shows a cross-sectional structure taken along line IIIC-IIIC shown in FIG. 3B (in the present specification, a Roman numeral "III" is used for convenience as a symbol corresponding to an Arabic numeral "3" shown in FIG. 3B). In FIG. 3A to FIG. 3D, for convenience of illustration, only one end side of the belt 20 is shown. However, the other end side also has an equivalent configuration.

The belt 20 is composed of a stretchable and insulating material. The both ends of belt 20 are respectively provided with the attachments 21 that connect to the supporting member 10 and the electrodes 30 that are respectively arranged near the attachments 21 (only one end side is shown in FIG. 3A to FIG. 3D), as shown in FIG. 3A to FIG. 3D, for example.

The attachment 21 is composed of a resin member or the like, and has locking tabs 22 that project in the longitudinal direction of the belt 20 (extending direction, or leftward direction in FIG. 3A to FIG. 3D), and a connection projecting section 23. The pair of locking tabs 22 have a flexible shape and are provided such that the pair of locking tabs 22 project in substantially parallel along the side portions in the width direction of the belt 20 (upper edge and lower edge in FIG. 3B). In order that the belt 20 is connected to the supporting member 10, the locking tabs 22 are pressed into the recessed engaging section 16 such that the respective tip portions are bent. The locking tabs 22 are then locked and fixed to the engaging section 16 by the return force of the tip portions back to its original state. On the other hand, in order that the belt 20 is detached from the supporting member 20, the attachment 21 is pulled out from the engaging section 16 in a state where the respective tip portions of the locking tabs 22 are bent and the locking tabs 22 are unlocked from the engaging section 16.

The connection projecting section 23 projects in a direction substantially parallel with the locking tabs 22 in, for example, the area between the pair of locking tabs 22 of the attachment 21, and is provided with a pipe 24 that supplies the fluid to the electrode 30 and a connection terminal 25 that is electrically connected to the electrode 30. The pipe 24 is composed of a soft resin member or the like, and is provided extending from the tip of the connection projecting section 23 of the attachment 21 to near the substantial center of the electrode 30. In a state where the attachment 21 is engaged with the engaging section 16, the tip portion of the pipe 24 pushes the control valve 18 open such that the control valve 18 becomes an open state. Then, the pipe 24 connects and communicates with the pipe 17 on the main body 11 side. At this time, the pipe 17 and the pipe 24 are connected in close contact with each other through the control valve 18. As a result the fluid does not leak out from the connected portion even when the fluid is supplied from the tank 12 through the pipe 17 and the pipe 24.

The connection terminal 25 is provided extending from the tip of the connection projecting section 23 of the attachment 21 towards the direction of the electrode 30, and is electrically connected to an electrode extending section 31 that is a portion of the electrode 30, described hereafter. The connection terminal 25 comes into contact with the above-described connection terminal 15 exposed within the engaging section 16 in a state where the attachment 21 is engaged with the engaging section 16. As a result, the connection terminal 25 and the connection terminal 15 are then electrically connected with each other.

The electrodes 30 are composed of a conductive fabric or rubber, a resin member, or the like, and are contained within the insulating belt 20, as shown in FIG. 3B to FIG. 3D. In addition, the electrodes 30 are configured to be exposed to a suitable position in the chest area of the measurement subject 100. Here, according to the present embodiment, the electrode 30 is provided such that the electrode 30 projects from the inner surface side (undersurface side in FIG. 3C) of the belt 20 towards the chest area (downward in FIG. 3C), as shown in FIG. 3C, for example. As a result, short-circuit between the electrodes 30 and the surroundings can be prevented, and, moreover, the electrodes 30 can be placed in favorable close contact with the chest area of the measurement subject 100. When conductive rubber, a resin member, or the like is used as the electrodes 30, the electrodes 30 are preferably configured to provide with fine holes or the like so as to allow the fluid supplied from the tank 12 of the main body 11 to flow between the electrodes 30 and the surface of the human, body.

The electrode extending section 31, which is a portion of the electrode 30 contained within the belt 20, extends in the direction of the end portion (leftward direction in FIG. 3A to FIG. 3D) of the belt 20, and is electrically connected to the connection terminal 25 of the attachment 21. As a result, the connection terminal 25 of the attachment 21 is electrically connected to the connection terminal 15 exposed within the engaging section 16 of the main body 11 in a state where the attachment 21 is engaged with the engaging section 16. Therefore, the pair of electrodes 30 exposed on the inner surface of the belt 20 are electrically connected to the circuit board 14 stored within the main body 11, via the connection terminals 25 and the connection terminals 15.

Figure 4:
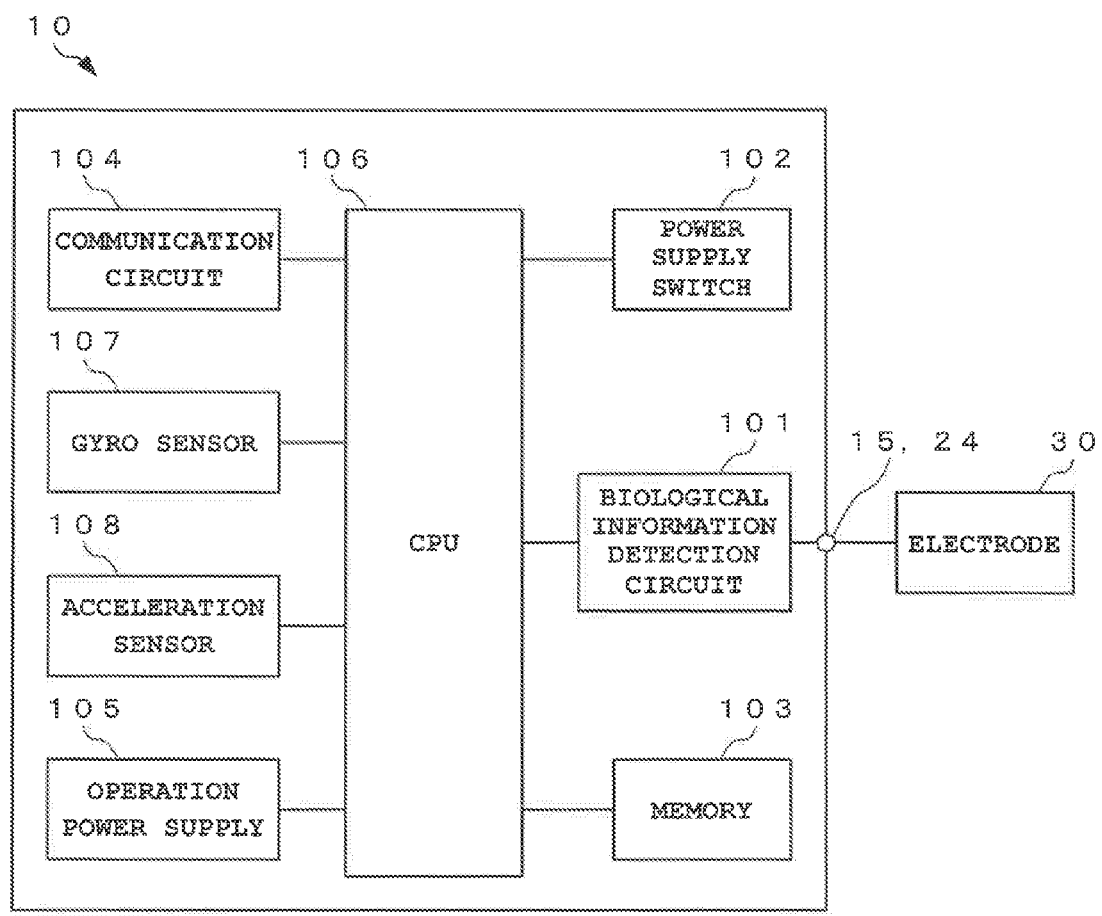
FIG. 4 is a functional block diagram of a configuration example of an electronic circuit contained in the supporting member according to the embodiment.

FIG. 4 is a functional block diagram of a configuration example of the electronic circuit contained in the supporting member 10 according to the present embodiment.

The supporting member 10 includes a biological information circuit 101; a power supply switch 102, a memory 103; a communication circuit 104; an operation power supply 105; a Central Processing Unit (CPU) 106; a gyro sensor (angular velocity sensor) 107; and an acceleration sensor 108, as shown in FIG. 4, for example.

The biological information circuit 101 is electrically connected to the pair of electrodes 30, via the connection terminals 15 provided in the main body 11 and the connection terminals 25 provided in the attachments 21 of the belt 20. The biological information circuit 101 detects biological information as an electric voltage variation pattern, where the electric voltage, variation pattern is received from the pair of electrodes 30 arranged to be in close contact with the chest area of the measurement subject 100, via the connection terminals 15 and the connection terminals 25. The detected biological information is stored as biological information data in a predetermined area of the memory 103.

The gyro sensor 107 measures the change of motion direction during exercise of the measurement subject 100 (angular velocity). The acceleration sensor 108 measures the rate of change of the motion velocity during exercise of the measurement subject 100 (acceleration) Exercise condition analysis data measured by the gyro sensor 107 and the acceleration sensor 108 are stored in a predetermined area of the memory 103 in association with the above-described biological information data detected by the biological information circuit 101.

The power supply switch 102 allows or interrupts the supply of power supply voltage supplied from the operation power supply 105 to each configuration, and controls ON and OFF of the power supply to the supporting member 10. According to the present embodiment, a slide switch or a push switch, which is provided on the top surface or a side portion (outer surface) of the main body 11, for example, can be used as the power supply switch 102 (not shown). As another aspects of the power supply switch 102, for example, the power can be turned ON when the attachments 21 of the belt 20 is connected to the main body 11 (in other words, when the biological information measuring device 1 is attached), and turned OFF when the attachment 21 is detached from the main body 11. Furthermore, as another aspect of the power supply switch 102, for example, the power can be turned ON at the same time the fluid is supplied from the tank 12 to the electrodes 30 by pressing the pressing section 13 provided in the main body 11, or after the elapse of a suitable amount of time (such as several seconds) from when the supply of fluid is started, and turned OFF by operating an OFF switch provided in the main body 11 separately from the pressing section 13.

The memory 103 has a non-volatile memory that mainly stores therein the biological information data detected by the biological information circuit 101 and the exercise condition analysis data measured by the gyro sensor 107 and the acceleration sensor 108. In addition, the memory 103 may also include a Read-Only Memory (ROM) that stores therein programs (software) for performing the various functions of the biological information circuit 101, the gyro sensor 107, the acceleration sensor 108, the memory 103, and the communication circuit 104. The CPU 106 actualizes the various functions of the biological information circuit 101, the gyro sensor 107, the acceleration sensor 108, the memory 103, and the communication circuit 104 by performing processing according to these programs. The programs may be loaded into the CPU 106 in advance. Alternatively, the non-volatile memory portion composed of the memory 103 may have a removable storage medium, such as a memory card, that can be detachably attached to the supporting member 10.

The communication circuit 104 functions as an interface for transmitting various data to an external device, such as a display device or an analysis device provided outside of the supporting member 10. The communication circuit 104 may transmit directly to the external device the biological information data detected by the biological information circuit 101 and the exercise condition analysis data measured by the gyro sensor 107 and the acceleration sensor 108, or may also transmit via the memory 103 to the external device the biological information data and the exercise condition analysis data after these data are stored in the memory 103. Here, for example, various wireless communication methods and infrared communication methods, as well as wired communication methods using communication cables, can be used as a method of transmitting the biological information data and the exercise condition analysis data to the external device via the communication circuit 104. As described detail hereafter, as well as a receiving terminal dedicated to the biological information measuring device, general-purpose mobile phones, multi-media devices, personal computers, and the like onto which software for analysis of the biological information data and the exercise condition analysis data is loaded can be used as the external device of such as a display device and an analysis device to which the biological information data and the exercise condition analysis data are transmitted from the supporting member 10.

(Attachment Method for the Biological Information Measuring Device)

Next, the attachment method for the biological information measuring device according to the present embodiment will be described.

Figure 5A:
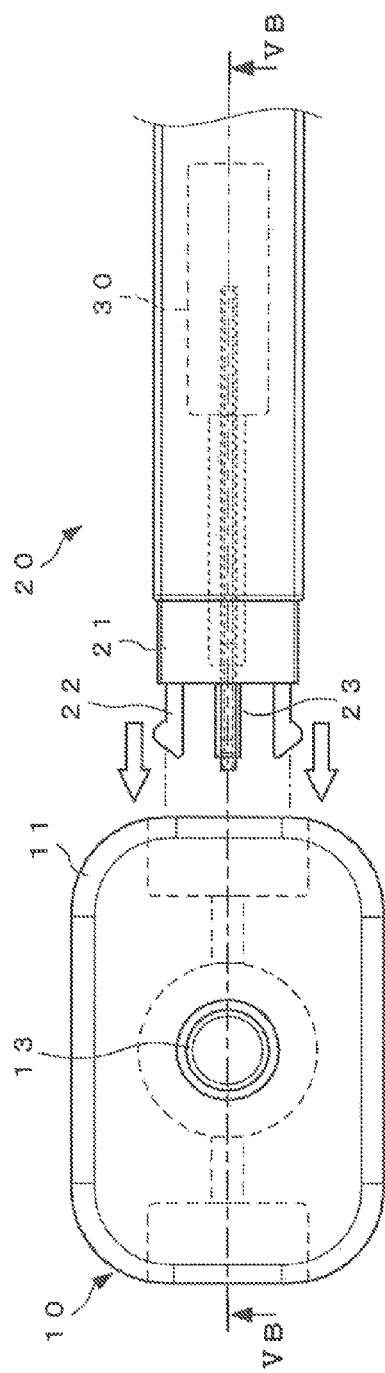
FIG. 5A to FIG. 5C are schematic diagrams of an attachment method (1) for the biological information measuring device according to the embodiment.
Figure 5B:
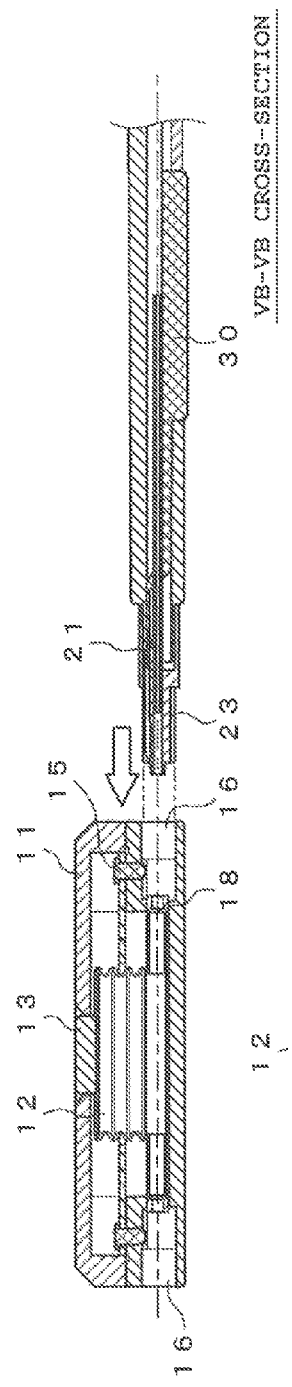
Figure 5C:
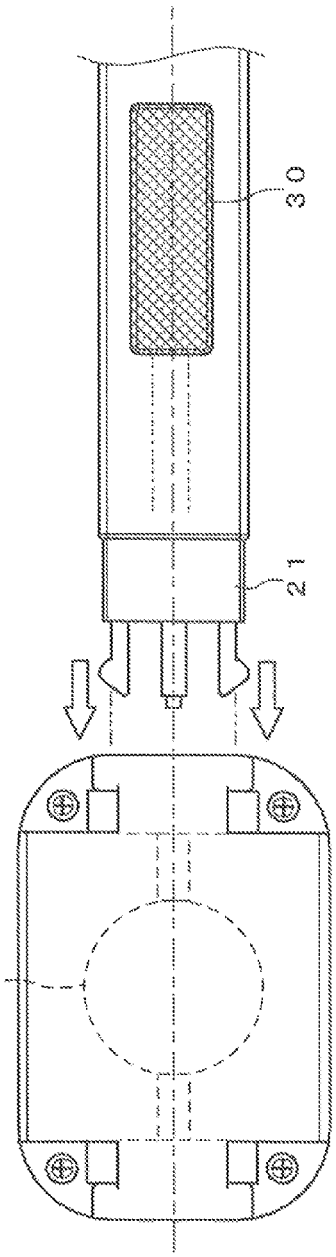
Figure 7A:
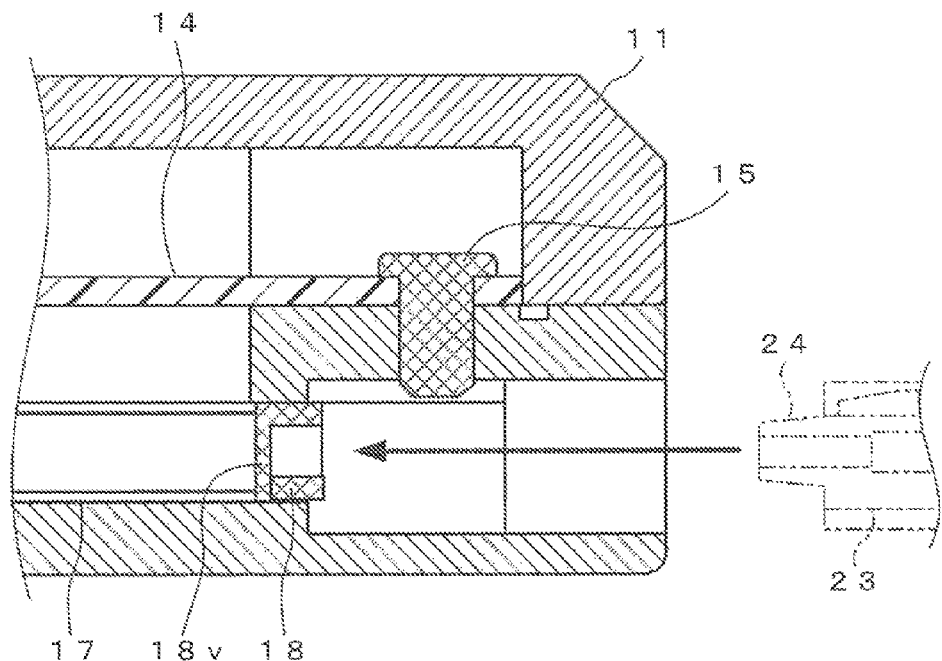
FIG. 7A and FIG. 7B are cross-sectional views of main sections showing the attachment method for the biological information measuring device according to the embodiment.
Figure 7B:
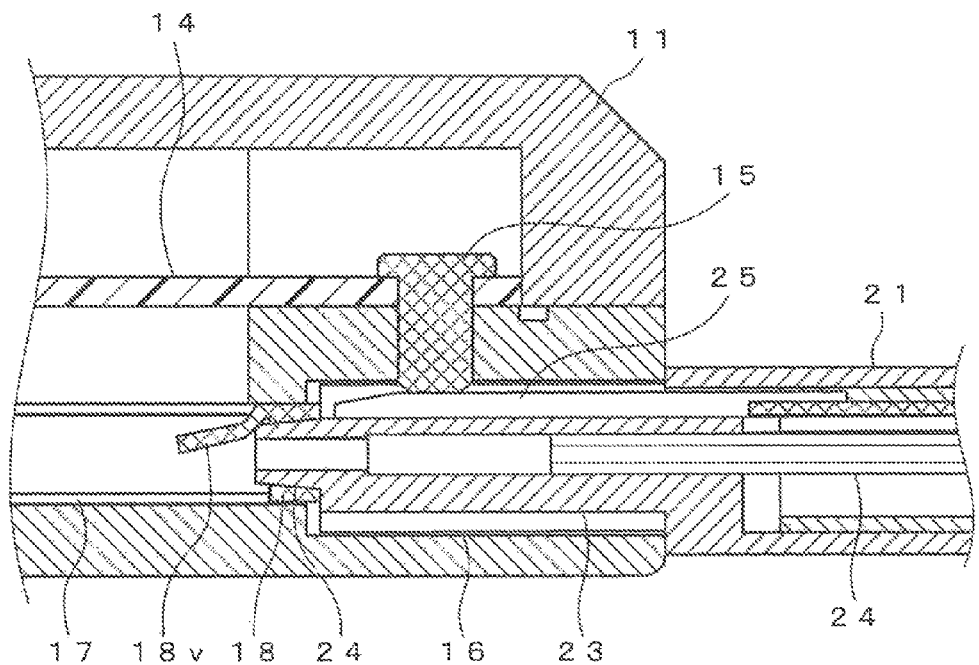
Figure 8:
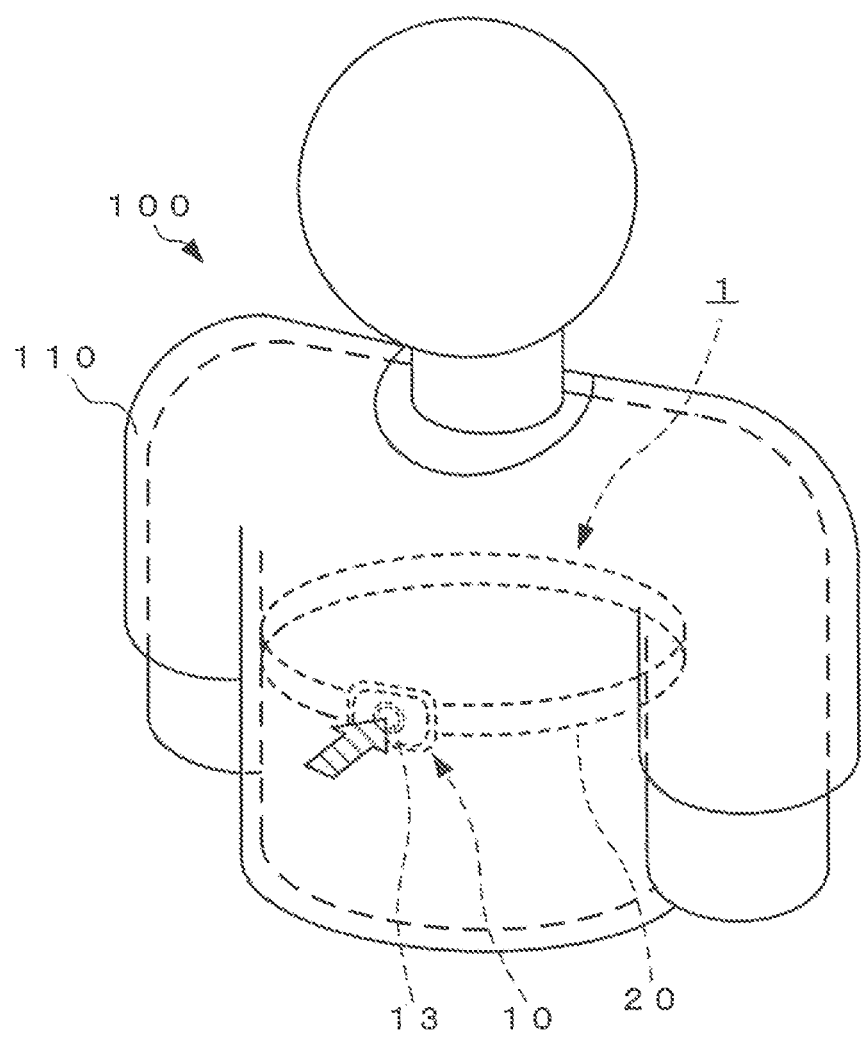
FIG. 8 is a conceptual diagram of a fluid supplying operation in the biological information measuring device according to the embodiment.
Figure 9:
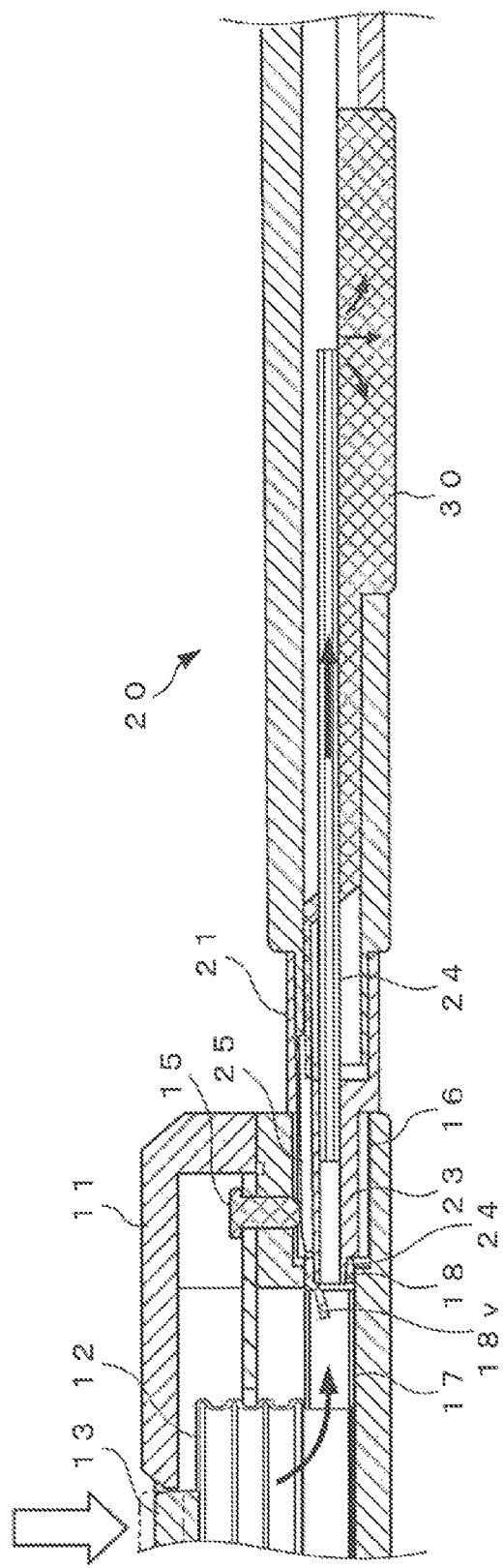
FIG. 9 is a cross-sectional view of main sections showing the fluid supplying operation in the biological information measuring device according to the embodiment.

FIG. 5A to FIG. 5C and FIG. 6A to FIG. 6C are schematic diagrams of the attachment method for the biological information measuring device 1 according to the present embodiment. FIG. 5A to FIG. 5C are detailed diagrams showing a state before the belt 20 is connected to the supporting member 10 according to the present embodiment. FIG. 5A is a top view. FIG. 5B is a cross-sectional view. FIG. 5C is a bottom view. FIG. 5B shows a cross-sectional structure taken along line VB-VB shown in FIG. 5A (in the present specification, a Roman numeral "V" is used for convenience as a symbol corresponding to an Arabic numeral "5" shown in FIG. 5A). FIG. 6A to FIG. 6C are detailed diagrams showing a state after the belt 20 is connected to the supporting member 10 according to the present embodiment. FIG. 6A is a top view. FIG. 6B is a cross-sectional view. FIG. 6C is a bottom view. FIG. 6B shows a cross-sectional structure taken along line VIB-VIB shown in FIG. 6A (in the present specification, a Roman numeral "VI" is used for convenience as a symbol corresponding to an Arabic numeral "6" shown in FIG. 6A). FIG. 7A and FIG. 7B are cross-sectional views of main sections showing the attachment method for the biological information measuring device 1 according to the present embodiment. FIG. 7A is a cross-sectional view of the main sections showing a state before the belt 20 is connected to the supporting member 10. FIG. 7B is a cross-sectional view of the main sections showing a state after the belt 20 is connected to the supporting member 10. FIG. 8 is a conceptual diagram of the fluid supplying operation in the biological information measuring device 1 according to the present embodiment. FIG. 9 is a cross-sectional view of the main sections showing the fluid supplying operation in the biological information measuring device 1 according to the present embodiment The attachment method for the biological information measuring device 1 configured as described above is basically performed by a series of procedures including a attaching operation, the fluid supplying operation, and a power ON operation. First, in the attaching operation, the attachments 21 of the belt 20 are engaged with the engaging sections 16 of the supporting member 10, whereby the supporting member 10 and the belt 20 are physically connected, as shown in FIG. 5A to FIG. 5C and FIG. 6A to FIG. 6C. Then, the belt 20 is wound around the chest area underneath the clothing 110 of the measurement subject 100, whereby the biological information measuring device 1 is attached in a state where the supporting member 10 and the pair of electrodes 30 are in direct contact with a suitable position in the chest area, as shown in FIG. 1A and FIG. 1B.

In the attaching operation, specifically, the locking tabs 22 of the attachments 21 are locked and fixed to the engaging sections 16, as shown in FIG. 7A and FIG. 7B. At this time, a valve 18v of each control valve 18 exposed within the respective engaging section 16 is pushed open by the tip portion of the pipe 24 provided in the connection projecting section 23 of the attachment 21, whereby the control valve 18 is set to an open state. Then, the pipes 17 on the main body 11 side and the pipes 24 on the attachment 21 side are connected by coming in close contact with each other via the control valves 18, thereby communicating with each other. At the same time, the connection terminal 25 provided in the connection projecting section 23 of each attachment 21 is electrically connected to the connection terminal 15 exposed within the respective engaging section 16.

Furthermore, the supporting member 10 is attached to the biological information measuring device 1 such that the supporting member 10 is in close contact with the chest area of the measurement subject 100. As a result, the body heat from the measurement subject 100 is transmitted through the enclosing cover 11c of the main body 11 of the supporting member 10 to the fluid within the tank 12, the pipes 17, and the pipes 24, whereby the temperature of the fluid is increased to a temperature close to body temperature.

Next, in the fluid supplying operation, the measurement subject 100 presses the pressing section 13 provided in the main body 11 of the supporting member 10 from the outside of the clothing 110, as shown in FIG. 8 (see arrow in FIG. 8). As a result, the pressure on the fluid stored within the tank 12 of the main body 11 increases, and whereby the fluid is supplied in the direction of the electrode 30 of the belt 20 through the pipe 17 and the pipe 24 that are connected with each other by the above-described attaching operation (see arrows in FIG. 9) For convenience of illustration, only one end side of the belt 20 is shown in FIG. 9. However, as in the case of the one end side of the belt 20, the fluid is supplied from the tank 12 through the pipe 17 and the pipe 24 to the electrode 30 on the other end side. After the fluid is reached the electrodes 30, the fluid permeates the electrodes 30 composed of a conductive fabric or rubber, a resin member, or the like, thereby allowing at least the surfaces of the electrodes 30 that are in direct contact with the chest area of the measurement subject 100 to be suitably wetted (or dampened). As a result, electrical resistance between the chest area of the measurement subject 100 and the electrodes 30 is reduced, and electrical conductivity can be sufficiently ensured. In addition, at this time, the fluid supplied to the electrodes 30 from the tank 12 is suitably heated by the body heat from the measurement subject 100 as a result of the above-described attaching operation. Therefore, even when the fluid permeates the electrodes 30 and reaches the surface of the chest area of the measurement subject 100, coldness of the fluid and discomfort experienced by the measurement subject 100 can be reduced or controlled.

Next, in the power ON operation, the measurement subject 100 operates, for example, a power supply switch (not shown) provided on the outer surface of the main body 11 of the supporting member 10, whereby the power of the supporting member 10 is turned. ON (set to an ON state). As a result detection of the biological information data and measurement of the exercise condition analysis data of the measurement subject 100 are started. In other words, based on an electric voltage variation pattern is received by the pair of electrodes 30 that are provided on the inner surface side (the human-body side when attached) of the belt 20 and in close contact with the chest area of the measurement subject 100, whereby the biological information is detected by the biological information circuit 101 provided in the circuit board 14, and then stored in the memory 103 as biological information data. At the same time, the exercise condition analysis data measured by the gyro sensor 107 and the acceleration sensor 108 is stored in the memory 103 in association with the biological information data.

As described above, in the attachment method for the biological information measuring device 1 according to the present embodiment, the belt 20 is connected to the supporting member 10, whereby the pipes 17 on the main body 11 side and the pipes 24 on the belt 20 side communicate. As a result, the fluid is supplied. Simultaneously at this time, the connection terminals 15 on the main body 11 side and the connection terminals 25 on the belt 20 side are electrically connected. As a result, the biological information data can be detected. Furthermore, the pressing section 13 provided in the supporting member 10 is pressed, whereby the fluid stored in the tank 12 is supplied to the electrodes 30 through the pipes 17 and the pipes 24. As a result, electrical resistance between the surface of the human body and the electrode 30 is reduced, and electrical conductivity is sufficiently ensured.

Therefore, according to the present embodiment, by simple operations of winding the belt around the chest area; attaching the biological information measuring device; and pressing the pressing section 13 provided in the main body 11 of the supporting member 10, the electrodes 30 provided in the belt 20 can be suitably wetted. As a result, the electrical resistance between the surface of the human body and the electrodes 30 can be reduced, and sufficient electrical conductivity can be ensured. Therefore, according to the present embodiment, the biological information during exercise of the measurement subject 100 can be accurately and unfailingly acquired, and the state of health and the exercise conditions can be accurately grasped. Generally, the operation for supplying fluid to the electrodes 30 by pressing the pressing section 13 of the main body 11 and wetting the electrodes 30 is only required to be performed once before exercise. It is because perspiration, water vapor, and the like are emitted from the surface of the human body not only during exercise, whereby the electrical resistance between the electrodes 30 and the chest area of the measurement subject 100 can be reduced by such moisture as well, and sufficient electrical conductivity can be ensured.

In addition, according to the present embodiment, the biological information measuring device 1 is attached in a state where the main body 11 of the supporting member 10 is in close contact with the chest area. As a result, the fluid within the tank 12 is heated by the body heat from the measurement subject 100. Therefore, even when the fluid is supplied from the tank 12 to the electrodes 30, unpleasantness and discomfort, such as coldness, experienced by the measurement subject 100 can be reduced or controlled.

Application Examples

The biological information measuring device 1 according to the above-described embodiment may be configured such that the detected biological information data can be displayed, analyzed, stored, and the like by a device provided outside of the supporting member 10.

Figure 10:
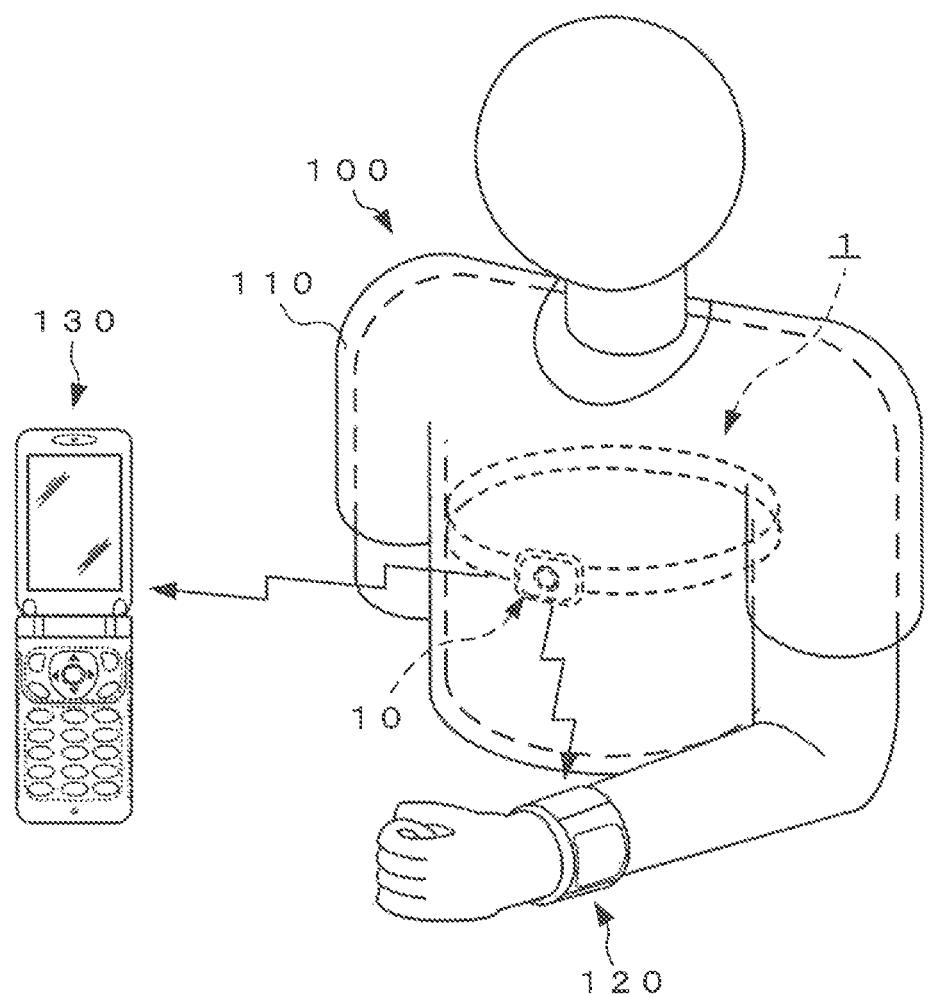
FIG. 10 is a conceptual diagram of a first configuration example of the biological information measuring device according to the embodiment in an instance where biological information data and exercise condition analysis data are transmitted.
Figure 11:
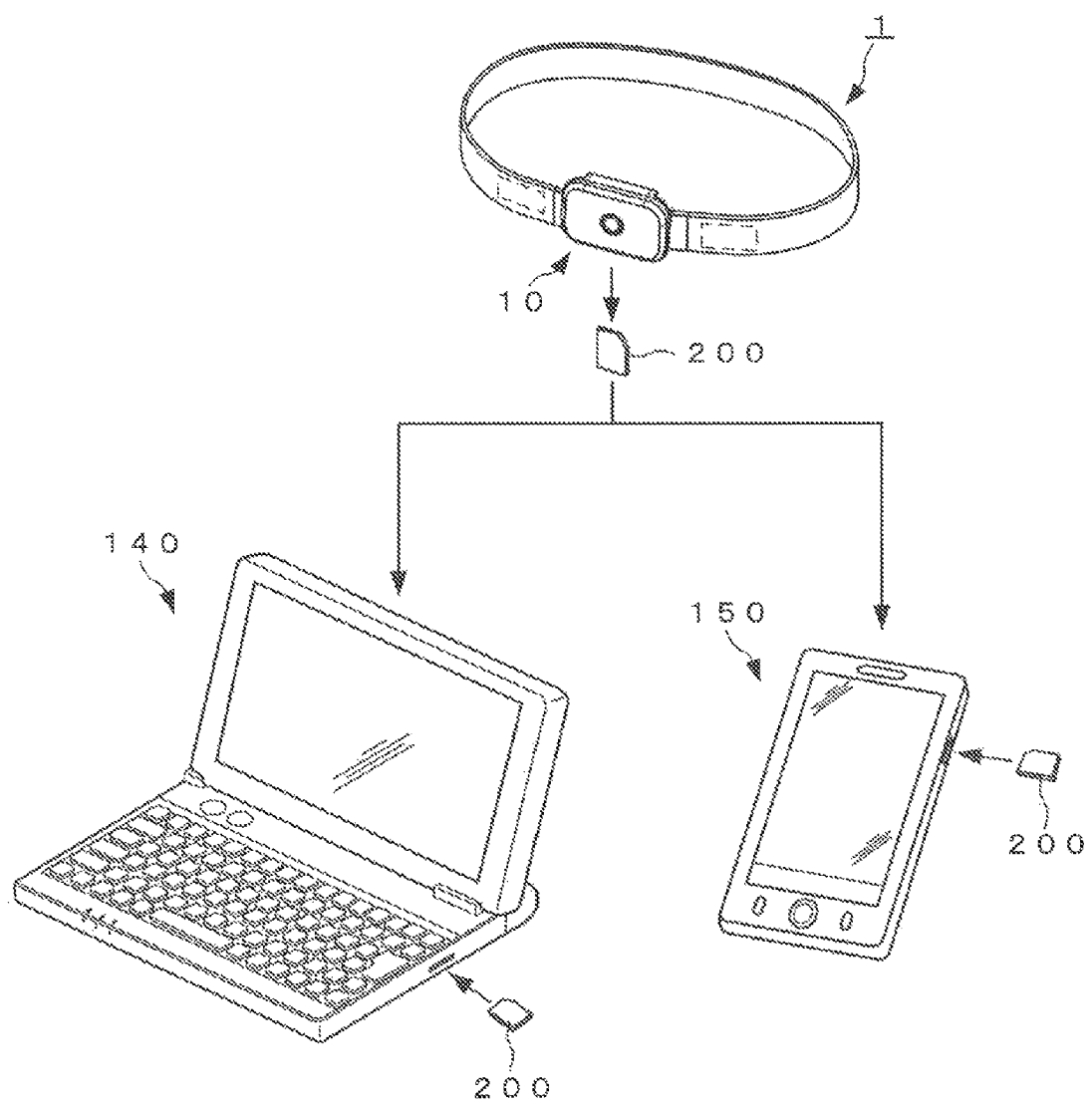
FIG. 11 is a conceptual diagram of a second configuration example of the biological information measuring device according to the embodiment in an instance, where biological information data and exercise condition analysis data are transmitted.

FIG. 10 is a conceptual diagram of a configuration example of the biological information measuring device 1 according to the present embodiment in an instance where the biological information data and the exercise condition analysis data are transmitted by a wireless method. FIG. 11 is a conceptual diagram of a configuration example of the biological information measuring device 1 according to the present embodiment in an instance where the biological information data and the exercise condition analysis data are transmitted by a memory card.

In the configuration example shown in FIG. 10, the biological information data detected by the biological information circuit 101 of the supporting member 10 and the exercise condition analysis data measured by the gyro sensor 107 and the acceleration sensor 108, or the biological information data and the exercise condition analysis data stored in the memory 103 are transmitted using a predetermined wireless communication method by the communication circuit 104 to a wristwatch-type or wristband-type dedicated receiving terminal 120 worn by the measurement subject 100 who attaches the biological information measuring device 1 according to the present embodiment, or a general-purpose mobile terminal 130, such as a mobile phone, a smartphone, or a multimedia player, carried by the measurement subject 100.

In this instance, the biological information data and the exercise condition analysis data acquired during exercise can be transmitted in real-time or immediately after exercise to the dedicated receiving terminal 120 or the mobile terminal 130, whereby the current biological information data and exercise condition analysis data, or analysis data based on these data and the like can be displayed in a display section. When the biological information data and the exercise condition analysis data, or the analysis data and the like are displayed using the general-purpose mobile terminal 130, software for analyzing the biological information data and the exercise condition analysis data or the like is required to be loaded onto the mobile terminal 130 in advance.

In addition, in the configuration example shown in FIG. 11, a removable storage medium 200, such as a memory card, is used as a non-volatile memory for storing the biological information data and the exercise condition analysis data in the memory 103 provided in the supporting member 10 of the biological information measuring device 1 according to the present embodiment. In this instance, the removable storage medium 200 is removed from the supporting member 10, and read by a personal computer 140, or a general-purpose mobile terminal 150, such as a mobile phone, a smartphone, or a multimedia player, whereby the biological information data and the exercise condition analysis data are transmitted (loaded).

As a result, the biological information data and the exercise condition analysis data, or the analysis data and the like can be displayed using the widespread general-purpose personal computer 140 and mobile terminal 150, without requiring a dedicated display device or analysis device. In addition, battery life can be significantly increased because a communication circuit with reduced power consumption is used or no communication circuit is required. In this instance as well, software for analyzing the biological information data and the exercise condition analysis data or the like is required to be loaded onto the personal computer 140 and the mobile terminal 150 in advance.

According to the above-described embodiment, the recessed engaging sections 16 are provided in the main body 11 of the supporting member 10, and the locking tabs 22 and the connection projecting sections 23 are provided such that the locking tabs 22 and the connection projecting sections 23 project from the attachments 21 on both end portions of the belt 20. However, the present invention is not limited thereto. In other words, the locking tabs and the connection projecting sections are provided such that the locking tabs and the connection projecting sections project from the main body 11 of the supporting member 10, and the recessed engaging sections are provided in the attachments 21 on both end portions of the belt 20. In addition, regarding the locking structure used for connecting the belt 20 to the supporting member 10, the present invention is not limited to the configuration using the locking tabs and the engaging sections according to the above-described embodiment. Other locking structures may be used. In addition, the attachment 21 can be provided in at least one end portion of the belt 20, and the attachment 21 can be provided in at least one of the belt 20 and the supporting member 10.

In addition, according to the above-described embodiment, the tank 12 provided in the main body 11 of the supporting member 10 is configured to have a cylindrical shape of which the side surface is formed into a bellows shape. However, the present invention is not limited thereto. The tank 12 may have another shape, such as a spherical shape or a dome shape. In addition, a sponge-like member may be stored within the tank 12 so as to hold the fluid therewithin.

Furthermore, according to the above-described embodiment, a method for refilling the tank 12 provided in the main body 11 of the supporting member 10 with the fluid is not particularly shown. However, the following method may be used: a dropper or the like having the same shape as the tip portion of the connection projecting section 23 provided in the attachment 21 is engaged with the valve 18*v* of the control valve 18 within the engaging section 16, and then the valve 18*v* is pushed open, whereby the tank 12 is refilled with fluid through the pipe 17.

In addition, according to the above-described embodiment, the pair of electrodes 30 provided on the inner surface side (the chest-area side when attached) of the belt 20 are shown as electrodes for detecting the biological information. However, the present invention is not limited thereto. In other words, the electrodes 30 of the present invention are merely required to be provided on the inner surface side of the belt 20 such that the electrodes 30 is in close contact with a suitable position of the chest area. The number of electrodes 30 is arbitrary and may be one, or three or more In addition, according to the above-described embodiment the supporting member 10 includes the gyro sensor 107 and the acceleration sensor 108 for acquiring the exercise condition analysis data are included as well as the biological information circuit 101 for acquiring the biological information data. However, the present invention is not limited thereto. Other sensors effective for analyzing the exercise conditions, such as a global positioning system (GPS) sensor, may also be included.

In addition, according to the above-described embodiment the biological information may be electrocardiographic signals, the biological information data may be heart rate data, and the biological information circuit may be a heart rate circuit.

While the present invention has been described with reference to the preferred embodiments, it is intended that the invention be not limited by any of the details of the description therein but includes all the embodiments which fall within the scope of the appended claims.

What is claimed is:

1. A biological information measuring device comprising:
   a belt which includes at least one electrode detecting a voltage based on biological information in accordance with contact between the at least one electrode and a human body;
   a supporting member which supports a tank where a predetermined fluid is stored;
   an attachment which attaches the belt to the supporting member and has a fluid supply portion supplying the fluid to the at least one electrode; and
   a biological information circuit which measures biological information based on the voltage detected by the at least one electrode.

2. The biological information measuring device according to claim 1, wherein the biological information circuit is provided inside of the supporting member.

3. The biological information measuring device according to claim 1, wherein the attachment is provided in at least one of the belt and the supporting member.

4. The biological information measuring device according to claim 1,
   wherein the attachment is provided in at least one end portion of the belt and the attachment further has a first terminal which is electrically connected to the electrode and a first pipe as the fluid supply portion which extends to the electrode,
   wherein the supporting member further has a second terminal which is connected to the biological information circuit and a second pipe which is connected to the tank, and
   wherein the first terminal and the second terminal are electrically connected and set in a state where the biological information is detectable by the electrode, and the first pipe and the second pipe are connected and the fluid within the tank is set in a state which is supplied to the electrode.

5. The biological information measuring device according to claim 4, wherein the supporting member has a pressure applying section which applies pressure to the tank, and the fluid within the tank is supplied to the electrode through the first pipe and the second pipe by pressure being applied to the tank.

6. The biological information measuring device according to claim 4,
   wherein the attachment has a projecting shape, and an engaging section of the supporting member has a recessed shape, and
   wherein the first terminal and the second terminal are electrically connected, and the first pipe and the second pipe are connected within the engaging section by the attachment being connected to the engaging section of the supporting member.

7. The biological information measuring device according to claim 6, wherein the supporting member has a control valve which controls supply of the fluid within the tank, and the control valve is opened, the first pipe and the second pipe are connected, and the fluid within the tank is supplied to the electrode by connecting the attachment to the engaging section of the supporting member.

8. The biological information measuring device according to claim 1, wherein the biological information is electrocardiographic signals and the biological information circuit is a heart rate circuit.

9. The biological information detecting device according to claim 1, wherein the biological information circuit further has an angular velocity sensor which measures change of motion direction of the human body, and an acceleration sensor which measures a rate of change of motion velocity of the human body, and exercise analysis data of the human body is measured by the angular velocity sensor and the acceleration sensor.

10. The biological information measuring device according to claim 7, wherein the fluid is supplied into the tank through the second pipe connected to the tank by opening the control valve provided in the engaging section of the supporting member.

11. An attachment method for a biological information measuring device, the biological information measuring device comprising: a belt which includes at least one electrode detecting a voltage based on biological information in accordance with contact between the at least one electrode and a human body; a supporting member which supports a tank where a predetermined fluid is stored; and an attachment which attaches the belt to the supporting member and has a fluid supply portion supplying the fluid to the at least one electrode; and the attachment method comprising:

connecting the belt, the attachment, and the supporting member to each other;

winding the belt around the human body such that the electrode and the supporting member are placed in contact with the human body; and setting the electrode in a state where the biological information is detectable, and setting the fluid within the tank in a state in which the fluid is supplied to the electrode by connecting the electrode to the supporting member.

12. The attachment method according to claim 11, wherein the attachment is provided in at least one end portion of the belt and the attachment further has a first terminal which is electrically connected to the electrode and a first pipe as the fluid supply portion which extends to the electrode, and wherein the supporting member further has a second terminal and a second pipe which is connected to the tank, the attachment method further comprising:

electrically connecting and setting the first terminal and the second terminal in a state where the biological information is detectable by the electrode, connecting the first pipe and the second pipe, and setting the fluid within the tank in a state in which the fluid is supplied to the electrode.

13. The attachment method according to claim 12, further comprising:

supplying the fluid within the tank to the electrode through the first pipe and the second pipe by applying pressure to the tank.

14. The attachment method according to claim 12, further comprising:

opening a control valve that controls supply of the fluid within the tank by connecting the first pipe and the second pipe, and supplying the fluid within the tank to the electrode by connecting the attachment to an engaging section of the supporting member.

15. The attachment method according to claim 14, further comprising:

increasing a temperature of the fluid within the tank by body heat from the human body as a result of the attachment being connected to the engaging section of the supporting member and the supporting member being attached such that the supporting member is in contact with the human body.

* * * * *

UNITED STATES PATENT AND TRADEMARK OFFICE
CERTIFICATE OF CORRECTION

| | | |
|---|---|---|
| PATENT NO. | : 9,113,842 B2 | Page 1 of 1 |
| APPLICATION NO. | : 13/787701 | |
| DATED | : August 25, 2015 | |
| INVENTOR(S) | : Hiroki Nishiyama | |

It is certified that error appears in the above-identified patent and that said Letters Patent is hereby corrected as shown below:

In the Claims:

Column 14, claim 9, line 51, delete "biological information detecting device"

and insert --biological information measuring device--.

Signed and Sealed this
Twenty-sixth Day of April, 2016

Michelle K. Lee
*Director of the United States Patent and Trademark Office*